United States Patent [19]

Shinohara et al.

[11] 4,124,640
[45] Nov. 7, 1978

[54] PROCESS FOR PRODUCING ALKOXYANILINES

[75] Inventors: Akira Shinohara, Shimizu; Kazuhito Akiyama, Shizuoka; Akira Miki, Fuji; Sadayoshi Matsui, Shimizu, all of Japan

[73] Assignee: Ihara Chemical Industry Co., Ltd., Tokyo, Japan

[21] Appl. No.: 736,335

[22] Filed: Oct. 28, 1976

[30] Foreign Application Priority Data

Mar. 1, 1976 [JP] Japan ................................ 51-21987
Mar. 17, 1976 [JP] Japan ................................ 51-28995

[51] Int. Cl.$^2$ .......................................... C07C 85/24
[52] U.S. Cl. ................................. 260/575; 260/577; 260/574
[58] Field of Search ............... 260/575, 612 D, DIG. 3

[56] References Cited

U.S. PATENT DOCUMENTS 3,709,939  1/1973  Dorman ........................ 260/612 D

OTHER PUBLICATIONS

Morrison et al., "Organic Chemistry", 2nd Ed., p. 492, (1966).
Astle, "Industrial Organic Nitrogen Compounds", p. 90, (1961).
Wagner & Zook, "Synthetic Organic Chemistry", pp. 226–228, (1953).
Smith et al., "Canadian Journal of Chemistry", vol. 47, pp. 2015–2019, (1969).

Primary Examiner—Winston A. Douglas
Assistant Examiner—John J. Doll
Attorney, Agent, or Firm—Oblon, Fisher, Spivak, McClelland & Maier

[57] ABSTRACT

Alkoxyanilines are produced by reacting a hydroxyaniline having the formula

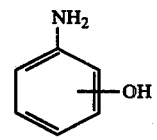

with an alkyl halide having the formula

R — X wherein R represents an alkyl group and X represents a halogen atom in the presence of an alkali metal alcoholate or hydroxide in a nonprotonic organic solvent selected from the group consisting of N-dimethyl acetamide, tetramethyl urea, hexamethylphosphoric triamide, dimethyl sulfoxide and N-methylpyrrolidone or a polyalkyleneglycol alkyl ether having the formula R'O (R"O)$_n$R' wherein R' represents an alkyl group having 1 to 4 carbon atoms and R" represents an alkylene group having 2 to 3 carbon atoms and n is an integer of 1 to 3.

8 Claims, No Drawings

PROCESS FOR PRODUCING ALKOXYANILINES

BACKGROUND OF THE INVENTION

The present invention relates to a process for producing alkoxyanilines which are useful as an intermediate for medicines and dyes and a raw material for various chemical compounds.

More particularly, it relates to a process for selectively producing alkoxyanilines in high yield and high efficiency by directly reacting hydroxyaniline with an alkyl halide.

It has been difficult to selectively produce the alkoxyaniline [I] by directly reacting hydroxyaniline with an alkyl halide because N-alkyl hydroxyaniline [a] and N-alkyl alkoxyaniline [b] have been formed as the by-products as shown in the following reaction formula [A].

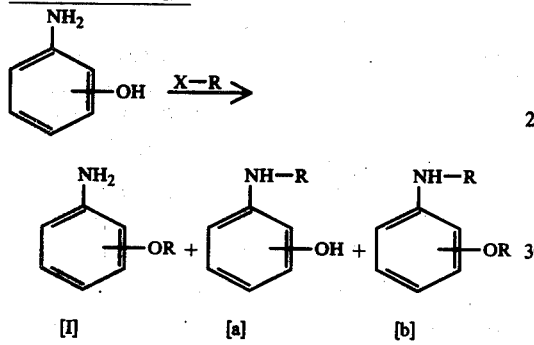

Accordingly, the alkoxyanilines have been produced by the process (1) which comprises protecting amino group (—$NH_2$) of hydroxyaniline as acetamide group (—$NHCOCH_3$) by an acetylation and then alkylating it with an alkyl halide and hydrolyzing it. [Journal of the Pharmaceutical Society of Japan Vol. 74 Pages 872 to 875 and Journal fur Prektische Chemie Vol. 4 No. 1 Pages 57 to 86 (1954)].

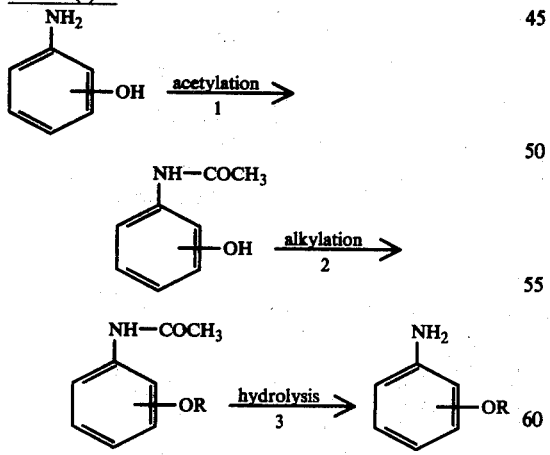

However, the steps of the acetylation and hydrolysis are included in the process (1) and accordingly, the reaction steps are complicated and many steps are needed whereby the cost of the alkoxyaniline is disadvantageously high, and the process is not satisfactory as the industrial process.

It has been studied to use the other alkylating agents instead of the alkyl halide.

As the result, it has been proposed to produce the alkoxyanilines by the process (2) which comprises converting hydroxyl group (—OH) of hydroxyaniline to sulfonic acid ester (—$OSO_2Ar$) with sulfochloride (Ar$SO_2Cl$) and using an alkali metal alcoholate (ROM) as the alkylating agent. [Journal of the Pharmaceutical Society of Japan Vol. 74 Pages 872 to 875 (1954) and Afinidad Organo de la Asocion de Quimicos Vol. 25 Pages 547 to 551 (1948)].

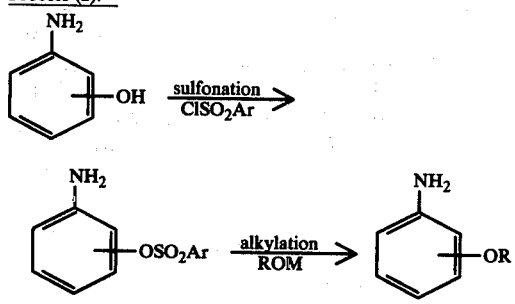

It has been also proposed to produce the alkoxyanilines by the process (3) which comprises directly alkylating hydroxyaniline with a dialkyl sulfate as the alkylating agent. [Journal of Organic Chemistry Vol. 22, Pages 333 to 334 (1957)].

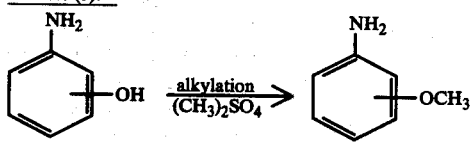

However, the sulfochlorides used in the process (2), react with an alcohol and phenol to produce sulfonic esters, and also react with ammonia, a primary amine or a secondary amine to produce sulfamides. Accordingly, in the case of hydroxyaniline having hydroxyl group and amino group, when the sulfochloride is used, the hydroxyl group of hydroxyaniline is converted to the sulfonic acid ester, and the amino group is converted to sulfamide at the same time, as shown in the following reaction formula (2'), whereby N-alkyl hydroxyaniline [a] and N-alkyl alkoxyaniline [b] are produced as the by-products.

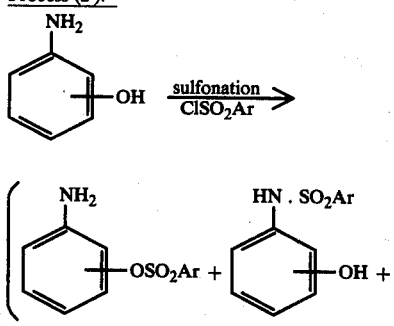

-continued

HN·SO₂Ar
[benzene ring with OSO₂Ar substituent] → alkylation / ROM →

[I] NH₂ / —OR  +  [a] NH—R / —OH  +  [b] NH—R / —OR

The sulfochlorides have stimulative smell and the alkali metal alcoholates as the alkylating agent are expensive and the operation for the reaction and the post-treatment are complicated as the industrial operation and the cost is disadvantageously high. Moreover, two steps are needed in the process (2).

In the process (3), the dialkyl sulfate used as the alkylating agent reacts as the alkylating agent for both of hydroxyl group and amino group whereby N-alkyl hydroxyaniline [a] and N-alkyl alkoxyaniline [b] are produced as the by-products.

Only dimethyl sulfate and diethyl sulfate are easily available as the dialkyl sulfates. Accordingly, the alkylations by the dialkyl sulfates are limited to methylation and ethylation, and it is not easy to give the alkylation for the alkyl group having 3 or more carbon atoms.

Usually, dialkyl sulfates have high toxicity. Though dimethyl sulfate is an active methylating agent, it is highly toxic, and it is not easy to use in the operation because the poisoning is caused by breathing the vapor and absorbing through the skin to cause dermatitis damages and mucous membrane damages.

As stated above, it has been difficult to selectively produce the alkoxyanilines by directly reacting hydroxyaniline with an alkyl halide. Accordingly, various processes have been proposed, however these conventional processes have not been satisfactory as the industrial process.

SUMMARY OF THE INVENTION

It is an object of the present invention to provide a process for producing alkoxyanilines in one step by using an alkyl halide which is easily available and economical, as the alkylating agent.

Another object of the invention is to provide a process for selectively producing alkoxyanilines in high yield by directly reacting hydroxyaniline with an alkyl halide while inhibiting the formation of N-alkyl hydroxyaniline and N-alkyl alkoxyaniline by-product.

These objects of the present invention have been attained by producing an alkoxyaniline having the formula

NH₂ / —OR  [I]

wherein R represents an alkyl group by directly reacting hydroxyaniline having the formula

NH₂ / —OH  [II]

with an alkyl halide having the formula

R — X   [III]

wherein R represents an alkyl group and X represents a halogen atom in the presence of an alkali metal alcoholate or hydroxide in a nonprotonic organic solvent selected from the group consisting of N-dimethyl acetamide, tetramethyl urea, hexamethylphosphoric triamide, dimethyl sulfoxide and N-methyl pyrrolidone or a polyalkyleneglycol alkyl ether having the formula

R'O(R"O)ₙR'   [IV]

wherein R' represents an alkyl group having 1 to 4 carbon atoms and R" represents an alkylene group having 2 to 3 carbon atoms and n is an integer of 1 to 3.

DETAILED DESCRIPTION OF THE EMBODIMENTS

The hydroxyanilines having the formula [II] used as the starting material in the process of the invention, include o-hydroxyaniline, m-hydroxyaniline and p-hydroxyaniline.

Suitably alkyl halides of formula [III] include alkyl fluorides, alkyl chlorides, alkyl bromides and alkyl iodides having a straight chain or branched chain alkyl group such as methyl, ethyl, n-propyl, iso-propyl, n-butyl, iso-butyl, sec-butyl, tert-butyl, n-amyl, iso-amyl, n-hexyl and n-heptyl group.

The bases used in the process of the invention are alkali metal alcoholates, and alkali metal hydroxides such as alcoholates e.g. sodium methylate, potassium methylate, sodium ethylate, potassium ethylate; and sodium hydroxide and potassium hydroxide and the like.

When an alkali metal hydroxide is used, it is preferable to add it in a form of powder or granules.

In the process of the invention, it is not preferable to use alkali metal carbonate or hydrogencarbonate instead of alkali metal alcoholate and hydroxide from the viewpoints of the selectivity and the yield.

The nonprotonic organic solvents used in the process of the invention as the reaction solvent, include N-dimethyl acetamide, tetramethyl urea, hexamethylphosphoric triamide <[CH₃)₂N]₃-P=O>, dimethyl sulfoxide, and N-methyl 2-pyrrolidone.

The polyalkyleneglycol alkyl ethers used in the process of the invention include the compounds shown in Table 1.

Table 1

| | |
|---|---|
| ethyleneglycol dimethyl ether | $CH_3OCH_2CH_2OCH_3$ |
| ethyleneglycol diethyl ether | $C_2H_5OCH_2CH_2OC_2H_5$ |
| diethyleneglycol dimethyl ether | $CH_3O$-$(CH_2CH_2O)_2$-$CH_3$ |
| diethyleneglycol dibutyl ether | $C_4H_9O$-$(CH_2CH_2O)_2$-$C_4H_9$ |
| triethyleneglycol dimethyl ether | $CH_3O$-$(CH_2CH_2O)_3$-$CH_3$ |
| triethyleneglycol diethyl ether | $C_2H_5O$-$(CH_2CH_2O)_3$-$C_2H_5$ |
| triethyleneglycol dibutyl ether | $C_4H_9O$-$(CH_2CH_2O)_3$-$C_4H_9$ |
| propyleneglycol dimethyl ether | $CH_3O-\underset{\underset{CH_3}{\mid}}{CH}CH_2O-CH_3$ |
| propyleneglycol diethyl ether | $C_2H_5O-\underset{\underset{CH_3}{\mid}}{CH}CH_2O-C_2H_5$ |

Table 1-continued

| | |
|---|---|
| dipropyleneglycol dimethyl ether | CH$_3$<br>\|<br>CH$_3$O—(CHCH$_2$O)$_{\overline{2}}$CH$_3$ |
| dipropyleneglycol diethyl ether | CH$_3$<br>\|<br>C$_2$H$_5$O—(CHCH$_2$O)$_{\overline{2}}$C$_2$H$_5$ |

In the process of the invention, it is not suitable to use an organic solvent which is not included in the above-mentioned definition. For example, when dimethyl formamide is used, as the solvent, side-reactions of dimethyl formamide with the hydroxyaniline [II] and the resulting alkoxyaniline [1] occur as shown in processes (4) and (5) thereby forming formamidine by-products.

Process (4):

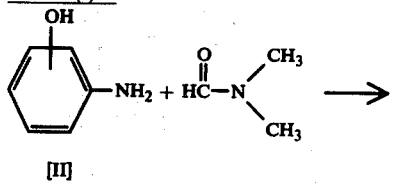

Process (5):

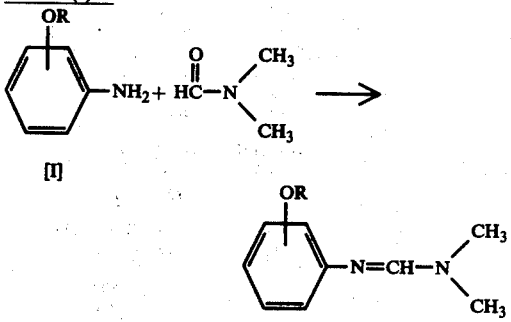

In an alcohol such as methanol, and ethanol, the reaction is performed however, the selectivity is too low and the yield is also low.

On the other hand, in a ketone such as acetone and methylethyl ketone, the alkoxyaniline is not obtained because of side reactions.

In a nitrile such as acetonitrile, and butyronitrile, the selectivity is high but the reaction velocity is too low and the yield of the alkoxyaniline is low.

In a nonpolar solvent such as benzene, toluene, xylene and hexane or a nonprotonic organic solvent of a cyclic ether such as tetrahydrofuran and dioxane, the yield of the alkoxyaniline [I] is not satisfactory because of low reaction velocity.

The reaction of the invention is performed by stirring the hydroxyaniline [II] and the alkyl halide [III] in the presence of the specific base in the specific nonprotonic organic solvent or the specific polyalkyleneglycol alkyl ether under heating.

Usually, the reaction is performed under atmospheric pressures and the reaction can be performed under higher pressure in an autoclave.

The reaction temperature is usually 50° to 200° C. preferably 70° to 100° C. When the reaction temperature is too high, the selectivity is low.

The ratio of the hydroxyaniline to the alkyl halide can be stoichiometrical mole ratio in the reaction. However, it is preferable to use excess of the alkyl halide in a range of 1.0 to 2.5 mole per 1 mole of the hydroxyaniline. It is preferable to use 1.0 to 2.0 moles of the specific base per 1 mole of the hydroxyaniline.

After the reaction, the resulting alkoxyaniline can be easily separated from the reaction mixture by distilling under a reduced pressure. The nonprotonic organic solvent or the polyalkyleneglycol alkyl ether used in the reaction, can be easily recovered by distilling under a reduced pressure.

The characteristics and advantages of the process of the invention will be illustrated.

(1) It is possible to selectively produce the alkoxyaniline by directly reacting the hydroxyaniline with the alkyl halide which has been considered to be difficult.

(2) It is possible to sufficiently prevent the formation of the by-product of N-alkyl hydroxyaniline and N-alkyl alkoxyaniline, whereby the alkoxyaniline can be obtained in high conversion and high selectivity and high yield.

The invention will be further illustrated by certain examples and references.

EXAMPLE 1

In a 500 ml autoclave made of glass, 150 ml of N-dimethyl acetamide, 15.2 g (0.3 mole) of methyl chloride, 8.8 g (0.22 mole) of sodium hydroxide and 21.8 g (0.2 mole) of o-hydroxyaniline were charged, and the reaction was carried out at 80° C. for 5 hours with stirring. During the reaction, the pressure in the autoclave was kept at 6.3 kg/cm$^2$.

After the reaction, the autoclave was cooled and the reaction mixture was filtered. A part of the filtrate was sampled and the components in the reaction mixture were measured according to the gas chromatography analysis.

The filtrate was concentrated under a reduced pressure to remove off N-dimethylacetamide by distillation and the residue was fractionally distilled to obtain 22.0 g of o-methoxyaniline having a boiling point of 115° to 117° C./19 mmHg. (yield: 89.5%).

According to gas chromatographic analysis, the ratio of o-methoxyaniline: N-methyl-o-hydroxyaniline: N-methyl-o-methoxyaniline in the reaction mixture was 94.2:0:5.8.

EXAMPLE 2

In a 500 ml of autoclave made of glass, 150 ml of ethylenglycol dimethyl ether, 15.1 g (0.3 mole) of methyl chloride, 42.4 g (0.22 mole) of sodium methylate in 28% methanol solution and 21.8 g (0.2 mole) of o-hydroxyaniline were charged and the reaction was carried out at 80° C. for 6 hours with stirring. During the reaction, the pressure in the autoclave was kept in 3 kg/cm$^2$.

After the reaction, the autoclave was cooled and the reaction mixture was filtered. A part of the filtrate was sampled and the components in the reaction mixture were measured according to the gas chromatography analysis.

The filtrate was concentrated under a reduced pressure to distill off ethyleneglycol dimethyl ether and the residue was fractionally distilled to obtain 16.6 g of o-methoxyaniline having a boiling point of 118° to 120° C./25 mmHg. (yield: 67.8%).

According to the gas chromatographic analysis, the ratio of o-methoxyaniline: N-methyl-o-hydroxyaniline: N-methyl-o-methoxyaniline in the reaction mixture was 96.6:0:3.4.

EXAMPLE 3

In accordance with the process of Example 1, 150 ml of dimethyl sulfoxide, 19.4 g (0.3 mole) of ethyl chloride, 8.8 g (0.22 mole) of sodium hydroxide and 21.8 g (0.22 mole) of p-hydroxyaniline were charged in the autoclave and the reaction was carried out at 80° C. for 5 hours with stirring to obtain 24.7 g of p-ethoxyaniline having a boiling point of 123.5° to 124.5° C./10 mmHg. (yield: 90.1%).

According to the gas chromatographic analysis, the ratio of p-ethoxyaniline: N-ethyl-p-hydroxyaniline: N-ethyl-p-ethoxyaniline in the reaction mixture was 94.7:0:5.3.

EXAMPLE 4

In accordance with the process of Example 2, 150 ml of diethyleneglycol dimethyl ether, 19.3 g (0.3 mole) of ethyl chloride, 42.2 g (0.22 mole) of sodium methylate in 28% methanol solution and 21.8 g (0.2 mole) of p-hydroxyaniline were charged in the autoclave and the reaction was carried out at 80° C. for 6 hours with stirring to obtain 19.7 g of p-ethoxyaniline having a boiling point of 135° to 136° C./24 mmHg. (yield: 72.1%).

According to the gas chromatographic analysis, the ratio of p-ethoxyaniline: N-ethyl-p-hydroxyaniline: N-ethyl-p-ethoxyaniline in the reaction mixture was 95.9:0:4.1.

EXAMPLE 5

In a 300 ml four necked flask equipped with a stirrer, a thermometer and a condenser, 150 ml of N-dimethyl acetamide, 39.3 g (0.5 mole) of iso-propyl chloride, 16.0 g (0.4 mole) of sodium hydroxide and 21.8 g (0.2 mole) of m-hydroxyaniline were charged and the reaction was carried out at 85° C. for 5 hours with stirring.

After the reaction, the reaction mixture was filtered. A part of the filtrate was sampled and the components in the reaction mixture were measured by gas chromatographic analysis.

The filtrate was concentrated under a reduced pressure to distill off N-dimethyl acetamide and the residue was fractionally distilled to obtain 28.9 g of m-iso-propoxyaniline having the boiling point of 136° to 138° C./25 mmHg. (yield: 93.4%).

According to gas chromatographic analysis, the ratio of m-iso-propoxyaniline: N-iso-propyl-m-hydroxyaniline: N-iso-propyl-m-iso-propoxyaniline in the reaction mixture was 98.0:0:2.0.

EXAMPLE 6

In a 300 ml four necked flask equipped with a stirrer, a thermometer and a condenser, 150 ml of diethyleneglycol dimethyl ether, 39.3 g (0.5 mole) of iso-propyl chloride, 77.1 g (0.4 mole) of sodium methylate in 28% methanol solution and 21.8 g (0.2 mole) of m-hydroxyaniline were charged and the reaction was carried out at 85° C. for 8 hours with stirring.

After the reaction, the reaction mixture was filtered. A part of the filtrate was sampled and the components in the reaction mixture were measured by gas chromatographic analysis.

The filtrate was concentrated under a reduced pressure to distill off diethyleneglycol dimethyl ether and the residue was fractionally distilled to obtain 21.6 g of m-iso-propoxyaniline having a boiling point of 137° to 138° C./23 mmHg. (yield: 71.5%).

According to the gas chromatography analysis, a ratio of m-iso-propoxyaniline: N-iso-propyl-m-hydroxyaniline: N-iso-propyl-m-iso-propoxyaniline in the reaction mixture was 96.0:0:4.0.

EXAMPLE 7

In accordance with the process of Example 5, 0.5 mole of isopropyl halide was reacted with 0.2 mole of m-hydroxyaniline in the presence of 0.4 mole of each base in 150 ml of each solvent. The results are shown in Table 2.

Table 2

$$\underset{OH}{\underset{|}{\bigcirc}}\text{-}NH_2 + \underset{H_3C}{\overset{H_3C}{\diagdown}}CH\text{-}X \xrightarrow{\text{base}}_{\text{solvent}} \underset{O-CH(CH_3)_2}{\underset{|}{\bigcirc}}\text{-}NH_2$$

| Test No. | X | Base | Solvent | Ratio of components in reaction mixture | | | Yield (%) |
|---|---|---|---|---|---|---|---|
| | | | | O | N | ON | |
| 1 | Br | NaOH | DMAC | 55.0 | 0 | 45.0 | 52.5 |
| 2 | Cl | CH₃ONa | DMAC | 98.1 | 0 | 1.9 | 85.0 |
| 3 | Cl | KOH | DMAC | 97.9 | 0 | 2.1 | 93.2 |
| 4 | Cl | NaOH | TMU | 96.1 | 0 | 3.9 | 84.8 |
| 5 | Cl | NaOH | MPD | 94.3 | 0 | 5.7 | 82.4 |
| 6 | Cl | NaOH | DMSO | 94.6 | 0 | 5.4 | 85.5 |
| 7 | Cl | C₂H₅ONa | HMPA | 89.3 | 0 | 2.2 | 84.3 |
| 8 | Br | NaOH | EGDM | 90.3 | 5.8 | 3.9 | 60.9 |
| 9 | Cl | CH₃ONa | DEGDM | 96.0 | 0 | 4.0 | 71.5 |
| 10 | Cl | KOH | DEGDM | 92.1 | 1.4 | 6.5 | 59.1 |
| 11 | Cl | NaOH | EGDM | 93.3 | 1.0 | 5.7 | 58.0 |
| 12 | Cl | NaOH | DEGDM | 93.2 | 1.1 | 5.7 | 60.7 |
| 13 | Cl | NaOH | TEGDM | 94.0 | 0.3 | 5.7 | 65.2 |
| 14 | Cl | C₂H₅ONa | DEGDM | 97.2 | 0 | 2.8 | 70.7 |
| Reference: | | | | | | | |
| 1 | Cl | NaOH | H₂O | 61.0 | 26.0 | 13.0 | 16.8 |
| 2 | Cl | NaOH | CH₃OH | 75.6 | 11.5 | 12.8 | 36.1 |
| 3 | Cl | NaOH | MIBK | no object product was obtained because of side reaction | | | |
| 4 | Cl | NaOH | AcNi | 97.6 | 0 | 2.4 | 15.0 |
| 5 | Cl | CH₃ONa | Ben | 93.4 | 0 | 6.6 | 10.9 |
| 6 | Cl | NaOH | Dio | 98.2 | 0 | 1.8 | 6.4 |

Note:
DMAC: N-dimethyl acetamide;
TMU: tetramethyl urea;
MPD: N-methyl-2-pyrrolidone;
DMSO: dimethyl sulfoxide;
HMPA: hexamethylphosphoric triamide;
EGDM: ethyleneglycol dimethyl ether;
DEGDM: diethyleneglycol dimethyl ether;
TEGDM: triethyleneglycol dimethylether;
MIBK: methylisobutyl ketone;
AcNi: acetonitrile;
Ben: benzene;
Dio: dioxane.

In the column of the ratio of components in the reaction mixture, the symbols are as follows.
O: m-isopropoxyaniline;
N: N-isopropyl-m-hydroxyaniline;
ON: N-isopropyl-m-isopropoxyaniline.

EXAMPLE 8

In a 300 ml four necked flask equipped with a stirrer, a thermometer and a condenser, 150 ml of N-dimethyl acetamide, 27.8 g (0.3 mole) of n-butyl chloride, 8.8 g (0.22 mole) of sodium hydroxide and 21.8 g (0.2 mole) of p-hydroxyaniline were charged and the reaction was carried out at 80° C. for 5 hours with stirring.

After the reaction, the reaction mixture was filtered. A part of the filtrate was sampled and the components in the reaction mixture were measured by gas chromatographic analysis.

The filtrate was concentrated under a reduced pressure to distill off N-dimethyl acetamide and the residue was fractionally distilled to obtain 30.7 g of p-n-butoxyaniline having a boiling point of 155° to 157° C./23 mmHg. (yield: 93.0%).

According to gas chromatographic analysis, a ratio of p-n-butoxyaniline: N-n-butyl-p-hydroxyaniline: N-n-butyl-p-n-butoxyaniline in the reaction mixture was 98.1:0:1.9.

EXAMPLE 9

In a 300 ml four necked flask equipped with a stirrer, a thermometer and a condenser, 150 ml of diethyleneglycol diethyl ether, 27.6 g (0.3 mole) of n-butyl chloride, 21.8 g (0.22 mole) of sodium methylate in 28% methanol solution and 21.8 g (0.2 mole) of p-hydroxyaniline were charged and the reaction of the mixture was carried out at 90° C. for 5 hours with stirring.

After the reaction, the reaction mixture was filtered. A part of the filtrate was sampled and the components in the reaction mixture were measured according to gas chromatographic analysis.

The filtrate was concentrated under a reduced pressure to distill off diethyleneglycol diethyl ether and the residue was fractionally distilled to obtain 24.3 g of p-n-butoxyaniline having a boiling point of 143° to 145° C./10 mmHg. (yield: 73.6%).

According to gas chromatographic analysis, a ratio of p-n-butoxyaniline: N-n-butyl-p-hydroxyaniline: N-n-butyl-p-n-butoxyaniline in the reaction mixture was 97.3:0:2.7.

EXAMPLE 10

In accordance with the process of Example 8, 0.3 mole of n-butyl halide was reacted with 0.2 mole of p-hydroxyaniline in the presence of 0.22 mole of sodium hydroxide in 150 ml of various nonprotonic organic solvents. The results are shown in Table 3.

Table 3

| Test No. | X | Solvent | Ratio of components in reaction mixture | | | Yield (%) |
|---|---|---|---|---|---|---|
| | | | O | N | ON | |
| 1 | Br | DMAC | 57.5 | 0 | 42.5 | 54.0 |
| 2 | Cl | TMU | 96.7 | 0 | 3.3 | 82.1 |
| 3 | Cl | MPD | 94.4 | 0 | 5.6 | 80.9 |
| 4 | Cl | DMSO | 94.5 | 0 | 5.5 | 86.1 |
| 5 | Cl | HMPA | 90.6 | 0 | 2.5 | 85.6 |

Note:
DMAC, TMU, MPD, DMSO and HMPA are shown in Table 2 of Example 7.

EXAMPLE 11

In accordance with the process of Example 9, 0.3 mole of n-butyl halide was reacted with 0.2 mole of p-hydroxyaniline in the presence of 28% methanol solution of 0.22 mole of sodium methylate in 150 ml of various polyalkyleneglycol alkyl ether. The results are shown in Table 4.

Table 4

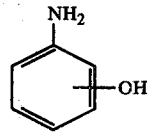

| Test No. | X | Solvent | Ratio of components in reaction mixture | | | Yield (%) |
|---|---|---|---|---|---|---|
| | | | O | N | ON | |
| 1 | Br | EGDM | 93.5 | 2.5 | 4.0 | 60.5 |
| 2 | Cl | " | 96.6 | 0 | 3.4 | 68.3 |
| 3 | Cl | DEGDM | 96.9 | 0 | 3.1 | 71.8 |
| 4 | Cl | TEGDM | 97.0 | 0 | 3.0 | 71.5 |
| 5 | Cl | DEGDP | 96.8 | 0 | 3.2 | 73.6 |

Note:
EGDM; DEGDM and TEGDM are shown in Table 2 of Example 7.
DEGDP: diethyleneglycol dipropyl ether As it is clear from the examples and the references, in accordance with the process of the invention, the alkoxyanilines are obtained in high selectivity and high efficiency and high yield while preventing the formation of by-products of N-alkyl hydroxyaniline and N-alkyl alkoxyaniline.

What is claimed is:

1. A process for producing an alkoxyaniline, which comprises: reacting a hydroxyaniline having the formula:

with an alkyl chloride having the formula RCl wherein R represents an alkyl group in the presence of an alkali metal alcoholate or hydroxide in a nonprotonic organic solvent selected from the group consisting of N-dimethylacetamide, tetramethylurea, hexamethylphosphoric triamide, N-methylpyrrolidone and a polyalkyleneglycolalkyl ether having the formula $R'O(R''O)_nR'$ wherein R' represents an alkyl group having 1 to 4 carbon atoms and R'' represents an alkylene group having 2 to 3 carbon atoms and n is an integer of 1 to 3.

2. The process according to claim 1, wherein said alkali metal alcoholate or hydroxide is sodium or potassium methylate, ethylate or hydroxide, and said alcoholate is in a form of an alcohol solution and said hydroxide is in a form of powder or granules.

3. The process according to claim 1, wherein said hydroxyaniline is o-hydroxyaniline, m-hydroxyaniline or p-hydroxyaniline and said group R is an alkyl group selected from the group consisting of methyl, ethyl, n-propyl, isopropyl, n-butyl, iso-butyl, sec-butyl, tert-butyl, n-amyl, iso-amyl, n-hexyl and n-heptyl groups.

4. The process according to claim 1, wherein the reaction is carried out at 50° to 200° C. under the atmospheric pressure or higher pressure.

5. The process according to claim 1, wherein an amount of the alkyl chloride is 1.0 to 2.5 moles per 1.0 mole of the hydroxyaniline and an amount of the alkali metal alcoholate or hydroxide is 1 to 2.0 moles per 1.0 mole of the hydroxyaniline.

6. The process according to claim 1, wherein the reaction is carried out in the nonprotonic organic solvent.

7. The process according to claim 1, wherein the reaction is carried out in a solvent of the polyalkyleneglycol alkyl ether.

8. The process of claim 1, wherein said non-protonic organic solvent is N-dimethylacetamide.

* * * * *